US012720009B2

(12) United States Patent
Choi et al.

(10) Patent No.: US 12,720,009 B2
(45) Date of Patent: Aug. 25, 2026

(54) ARTIFICIAL INTELLIGENCE SURGICAL SYSTEM AND CONTROL METHOD THEREFOR

(71) Applicant: HUTOM INC., Seoul (KR)

(72) Inventors: Min Kook Choi, Seoul (KR); Chi Hyun Song, Seoul (KR); Hyun Hee Yoo, Seoul (KR); Sung Jae Kim, Seoul (KR)

(73) Assignee: HUTOM INC., Seoul (KR)

( * ) Notice: Subject to any disclaimer, the term of this patent is extended or adjusted under 35 U.S.C. 154(b) by 0 days.

(21) Appl. No.: 18/409,033

(22) Filed: Jan. 10, 2024

(65) Prior Publication Data

US 2024/0223722 A1 Jul. 4, 2024

Related U.S. Application Data

(63) Continuation of application No. PCT/KR2022/009481, filed on Jun. 30, 2022.

(30) Foreign Application Priority Data

Jul. 12, 2021 (KR) ........................ 10-2021-0090786

(51) Int. Cl.

| | |
|---|---|
| ***H04N 5/91*** | (2006.01) |
| ***A61B 6/50*** | (2024.01) |
| ***A61B 34/00*** | (2016.01) |
| ***A61B 34/20*** | (2016.01) |
| ***A61B 34/30*** | (2016.01) |
| ***A61B 90/00*** | (2016.01) |

(Continued)

(52) U.S. Cl.
CPC ............... *H04N 5/91* (2013.01); *A61B 6/504* (2013.01); *G06V 10/778* (2022.01); *G06V 20/41* (2022.01)

(58) Field of Classification Search
None
See application file for complete search history.

(56) References Cited

U.S. PATENT DOCUMENTS 10,791,301 B1 * 9/2020 Garcia Kilroy ........ G11B 27/10
11,185,388 B2 11/2021 Kim (Continued)

FOREIGN PATENT DOCUMENTS

CN 110996748 A 4/2020
KR 10-1862360 B1 6/2018

(Continued)

OTHER PUBLICATIONS

Office Action issued in KR 10-2021-0090786; mailed by the Korean Intellectual Property Office on Dec. 19, 2022.

(Continued)

*Primary Examiner* — Hung Q Dang
(74) *Attorney, Agent, or Firm* — Studebaker Brackett PLLC

(57) ABSTRACT

Disclosed are an artificial intelligence surgical system and a control method therefor. The artificial intelligence surgical system includes a recording device that records a surgical process as a video and inputs the recorded video to a pre-trained artificial intelligence algorithm to determine a (Continued)

surgical stage, and a server that updates the pre-trained artificial intelligence algorithm of the recording device by using the video received from the recording device.

7 Claims, 3 Drawing Sheets

(51) Int. Cl.

| | |
|---|---|
| ***G06N 3/08*** | (2023.01) |
| ***G06N 20/00*** | (2019.01) |
| ***G06V 10/778*** | (2022.01) |
| ***G06V 20/40*** | (2022.01) |
| ***G16H 20/40*** | (2018.01) |
| ***G16H 30/20*** | (2018.01) |
| ***G16H 30/40*** | (2018.01) |
| ***G16H 40/63*** | (2018.01) |
| ***G16H 40/67*** | (2018.01) |

(56) References Cited

U.S. PATENT DOCUMENTS

| | | | | |
|---|---|---|---|---|
| 2006/0241465 | A1* | 10/2006 | Huennekens | A61B 5/06 600/458 |
| 2008/0275467 | A1* | 11/2008 | Liao | A61B 90/36 703/11 |
| 2018/0028079 | A1* | 2/2018 | Gurevich | A61B 5/7232 |
| 2018/0322961 | A1* | 11/2018 | Kim | G16H 50/20 |
| 2019/0223961 | A1 | 7/2019 | Barral et al. | |
| 2019/0362834 | A1* | 11/2019 | Venkataraman | G06V 20/41 |
| 2020/0357502 | A1 | 11/2020 | Lee et al. | |
| 2020/0375662 | A1 | 12/2020 | Lee et al. | |
| 2021/0282892 | A1 | 9/2021 | Kim | |
| 2022/0019804 | A1* | 1/2022 | Gubbi Lakshminarasimha | G06V 20/46 |
| 2022/0233253 | A1* | 7/2022 | Shelton, VI | G16H 40/20 |
| 2022/0409326 | A1* | 12/2022 | Wright | G06V 10/82 |

FOREIGN PATENT DOCUMENTS

| | | | |
|---|---|---|---|
| KR | 10-2019-0088375 | A | 7/2019 |
| KR | 10-2013814 | B1 | 8/2019 |
| KR | 10-2020-0068355 | | 6/2020 |
| KR | 10-2020-0096155 | | 8/2020 |
| WO | 2019/132168 | A1 | 7/2019 |
| WO | 2021/010985 | A1 | 1/2021 |

OTHER PUBLICATIONS

Bernd Münzer et al.; "Relevance Segmentation of Laparoscopic Videos"; 2013 IEEE International Symposium on Multimedia; IEEE Computer Society; Dec. 9-11, 2013; pp. 84-91.

T. Syeda-Mahmood et al.; "Automatic Selection of Keyframes from Angiogram Videos"; 2010 20th International Conference on Pattern Recognition; IEEE Computer Society; Aug. 23-26, 2010; pp. 4008-4011.

International Search Report issued in PCT/KR2022/009481; mailed Oct. 13, 2022.

Extended European Search Report issued in EP 22 84 2339.8-1122 by the European Patent Office on Sep. 30, 2024, which is related to U.S. Appl. No. 18/409,033.

* cited by examiner

ARTIFICIAL INTELLIGENCE SURGICAL SYSTEM AND CONTROL METHOD THEREFOR

CROSS-REFERENCE TO RELATED APPLICATIONS

The present application is a continuation of International Patent Application No. PCT/KR2022/009481, filed on Jun. 30, 2022, which is based upon and claims the benefit of priority to Korean Patent Application No. 10-2021-0090786 filed on Jul. 12, 2021. The disclosures of the above-listed applications are hereby incorporated by reference herein in their entirety.

BACKGROUND

Embodiments of the present disclosure described herein relate to an artificial intelligence surgical system and a control method therefor.

During a surgical process, there is a need for the development of technologies capable of providing information to assist doctors in surgery. To provide the information to assist surgery, the surgical operation needs to be recognized.

Accordingly, there is a need for the development of technology that allows computers to recognize surgical actions from surgical images.

Moreover, deep learning is being widely used to analyze medical images nowadays. The deep learning is defined as a set of machine learning algorithms that attempt high-level abstractions (a task of summarizing key content or functions in large amounts of data or complex materials) through a combination of several nonlinear transformation techniques. The deep learning may be roughly classified as a field of machine learning that teaches a person's mindset to computers.

SUMMARY

Embodiments of the present disclosure provide an artificial intelligence surgical system capable of providing a video related to surgery in an optimized manner by using an artificial intelligence model, and a control method therefor.

Problems to be solved by the present disclosure are not limited to the problems mentioned above, and other problems not mentioned will be clearly understood by those skilled in the art from the following description.

According to an embodiment, an artificial intelligence surgical system includes a recording device that records a surgical process as a video and inputs the recorded video to a pre-trained artificial intelligence algorithm to determine a surgical stage, and a server that updates the pre-trained artificial intelligence algorithm of the recording device by using the video received from the recording device.

In this case, the recording device may delete a video portion, in which a non-surgical situation is recorded, from the recorded video by using the pre-trained artificial intelligence algorithm.

Moreover, the recording device may selectively record an angiographic image by using the pre-trained artificial intelligence algorithm.

Furthermore, the recording device may infer a surgical stage corresponding to the recorded video by using the pre-trained artificial intelligence algorithm, may link the recorded video with the inferred surgical stage based on the inferred surgical stage, and may link the recorded video with the inferred surgical stage when the inferred surgical stage is a surgical stage requiring vascular and organ matching.

Also, the recording device may pause recording of the video while linking the recorded video with the inferred surgical stage.

Besides, the recording device may segment the recorded video, and may transmit at least part of the segmented video to the server. In addition, the server may update the pre-trained artificial intelligence algorithm by using at least part of the segmented video received from the recording device, and may transmit the updated pre-trained artificial intelligence algorithm to the recording device.

According to an embodiment, a control method of an artificial intelligence system including a recording device and a server includes recording, by the recording device, a surgical process as a video, inputting, by the recording device, the recorded video to a pre-trained artificial intelligence algorithm and determining a surgical stage, linking, by the recording device, the recorded video to the determined surgical stage when it is determined that the determined surgical stage is a predetermined surgical stage, transmitting, by the recording device, at least part of the recorded video to the server, and updating, by the server, the pre-trained artificial intelligence algorithm of the recording device by using the video received from the recording device.

According to an embodiment, a computer program may be stored in a computer-readable recording medium in combination with a computer that is a piece of hardware to execute the control method of an artificial intelligence surgical system.

Other details according to an embodiment of the present disclosure are included in the detailed description and drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
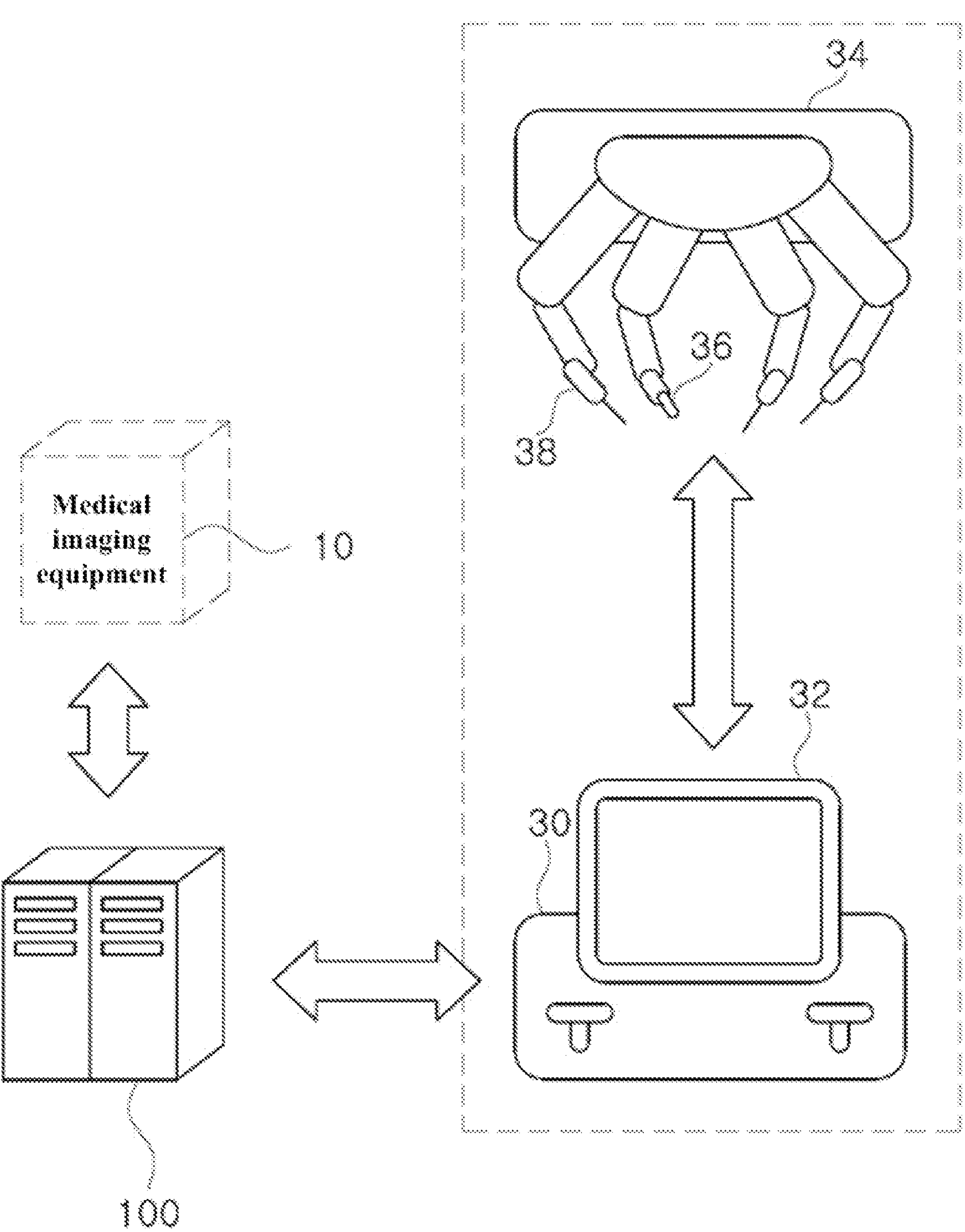
FIG. 1 is a conceptual diagram for describing an artificial intelligence surgical system, according to an embodiment of the present disclosure.

The above and other aspects, features and advantages of the present disclosure will become apparent from embodiments to be described in detail in conjunction with the accompanying drawings. The present disclosure, however, may be embodied in various different forms, and should not be construed as being limited only to the illustrated embodiments. Rather, these embodiments are provided as examples so that the present disclosure will be thorough and complete, and will fully convey the scope of the present disclosure to those skilled in the art. The present disclosure may be defined by the scope of the claims.

The terms used herein are provided to describe embodiments, not intended to limit the present disclosure. In the specification, the singular forms include plural forms unless particularly mentioned. The terms “comprises” and/or “comprising” used herein do not exclude the presence or addition of one or more other components, in addition to the aforementioned components. The same reference numerals denote the same components throughout the specification. As used herein, the term “and/or” includes each of the associated components and all combinations of one or more of the associated components. It will be understood that, although the terms “first”, “second”, etc., may be used herein to describe various components, these components should not be limited by these terms. These terms are only used to distinguish one component from another component. Thus, a first component that is discussed below could be termed a second component without departing from the technical idea of the present disclosure.

Unless otherwise defined, all terms (including technical and scientific terms) used herein have the same meaning as commonly understood by those skilled in the art to which the present disclosure pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, embodiments of the present disclosure will be described in detail with reference to accompanying drawings.

FIG. 1 is a conceptual diagram for describing an artificial intelligence surgical system, according to an embodiment of the present disclosure.

According to FIG. 1, an artificial intelligence surgical system (or a robot surgical system) according to an embodiment of the present disclosure includes medical imaging equipment 10, a server 100, and a recording device 30, a display 32, and a surgical robot 34, which are provided in an operating room. According to an embodiment, the medical imaging equipment 10 may be omitted in the artificial intelligence surgical system according to the disclosed embodiment.

The surgical robot 34 includes a shooting device 36 and a surgical instrument 38.

The recording device 30 may control the surgical robot 34 to perform robotic surgery.

The robotic surgery is performed as a user controls the surgical robot 34 by using the recording device 30. In an embodiment, the robotic surgery may be automatically performed by the recording device 30 without the control of the user.

In this specification, the recording device 30 and the surgical robot 34 are described as being separated from each other, but are not limited thereto. The surgical robot 34 may be included in the recording device 30 and may be controlled as a component of the recording device 30.

The server 100 is a computing device including at least one processor and a communication unit.

The recording device 30 includes the computing device including the at least one processor and the communication unit. In an embodiment, the recording device 30 includes hardware and software interfaces for controlling the surgical robot 34.

The shooting device 36 includes at least one image sensor. That is, the shooting device 36 is used to photograph an object, that is, a surgical site, by including at least one camera device. In an embodiment, the shooting device 36 includes at least one camera coupled with a surgical arm of the surgical robot 34.

In an embodiment, an image captured by the shooting device 36 is displayed on the display 32.

In an embodiment, the surgical robot 34 includes one or more surgical instruments 38 capable of performing cutting, clipping, fixing, catching operations, or the like of a surgical site. The surgical instrument 38 is used in combination with the surgical arm of the surgical robot 34.

The recording device 30 receives information necessary for surgery from the server 100 or generates information necessary for surgery and provides the information to the user. For example, the recording device 30 displays information, which is generated or received and which is necessary for surgery on the display 32.

For example, the user performs robotic surgery by operating the recording device 30 while the user watches the display 32 and controlling the movement of the surgical robot 34.

The server 100 generates information necessary for robotic surgery by using medical image data of an object previously photographed from the medical imaging equipment 10, and provides the generated information to the recording device 30.

The recording device 30 provides information to the user by displaying information received from the server 100 on the display 32; alternatively, the recording device 30 controls the surgical robot 34 by using information received from the server 100.

In an embodiment, the means capable of being used in the medical imaging equipment 10 is not limited thereto. For example, various other medical image acquisition means such as CT, X-Ray, PET, and MRI may be used.

In an embodiment, the surgical image obtained from the shooting device 36 is delivered to the recording device 30.

In an embodiment, the recording device 30 may segment a surgical image obtained during surgery in real time.

In an embodiment, the recording device 30 transmits the surgical image to the server 100 during surgery or after surgery is completed.

The server 100 may receive and analyze the surgery image.

The server 100 trains and stores at least one model for analyzing the surgical image.

The server 100 uses learning data to learn at least one model, and the learning data includes, but is not limited to, surgery images and information about the surgery images.

Embodiments disclosed below may not be applicable only in connection with the artificial intelligence surgical system shown in FIG. 1. The present disclosure may be applied to all types of embodiments of performing learning by using surgical images and recognizing specific operations through the learned results.

Moreover, hereinafter, for convenience of description, a “computer” will be described as performing the learning-based surgical operation recognizing method according to an embodiment disclosed herein. The “computer” may mean the server 100 or the recording device 30 in FIG. 1, but is not limited thereto and may be used to include devices capable of performing computing processing.

Figure 2:
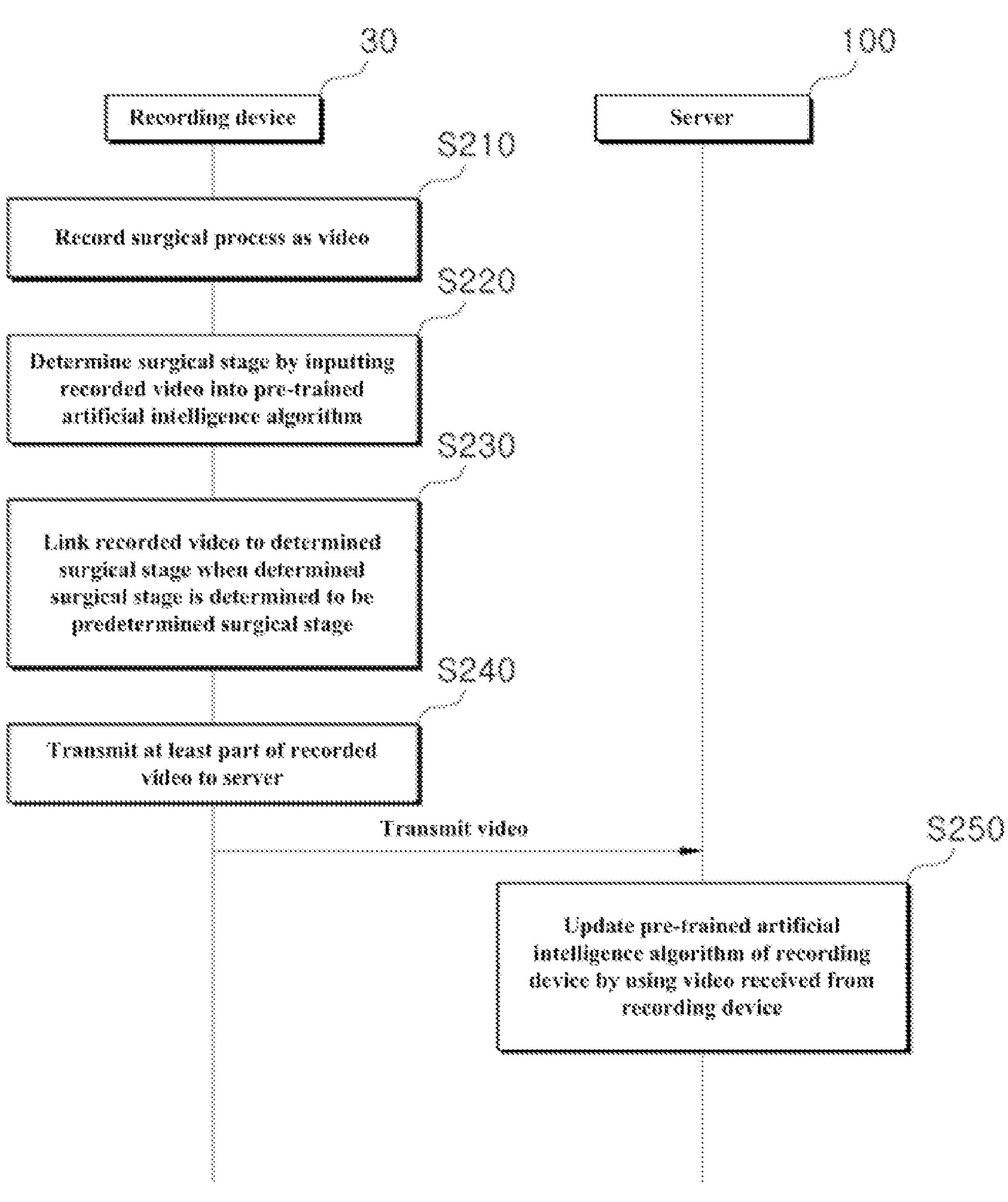
FIG. 2 is a flowchart for describing a control method of an artificial intelligence surgical system, according to an embodiment of the present disclosure.

FIG. 2 is a flowchart for describing a control method of an artificial intelligence surgical system, according to an embodiment of the present disclosure.

The artificial intelligence surgical system according to an embodiment of the present disclosure may include the recording device 30 and the server 100. The control method of the artificial intelligence surgical system according to an embodiment of the present disclosure may be controlled by the recording device 30 and the server 100.

The recording device 30 may record a surgical process as a video (or surgical image) (S210).

The surgical image may be an actual surgical image or a virtual image for simulation.

The actual surgical image may refer to data obtained as medical staff actually perform surgery and may be, for example, an image of an actual surgery scene actually performed by the surgical robot 34.

In other words, the actual surgical image is data obtained by recording a surgical site and surgical operations in an actual surgical process.

The virtual image for simulation refer to a simulation image created based on medical images taken from the medical imaging equipment 10, and may be, for example, a simulation model created by modeling a medical image of an actual patient in three-dimension (3D).

In this case, a virtual surgical image may be created by performing rehearsal or simulation on the simulation model in virtual space. Accordingly, the virtual image may be data obtained by recording the surgical site and surgical operation in the surgical process performed on the simulation model.

Furthermore, the surgical image may include one or more image frames.

Each image frame may include part of the patient's body, that is, the surgical site.

Besides, each image frame may include not only the patient's surgical site, but also surgical instruments and consumables required for surgery. In other words, a surgical image refers to data composing of video frames obtained by recording surgical operations for each scene over time in the surgical process.

Accordingly, data composed of these video frames may be referred to as a surgical image sequence.

The recording device 30 may determine (or infer) a surgical stage by inputting the recorded video into a pre-trained artificial intelligence algorithm (S220).

The pre-trained artificial intelligence algorithm may refer to an artificial intelligence model learned based on deep learning, and may refer to, for example, an algorithm trained by using a convolutional neural network (CNN).

Besides, the pre-trained artificial intelligence algorithm may include at least one algorithm among Random Forest (RF), Support Vector Machine (SVC), eXtra Gradient Boost (XGB), Decision Tree (DT), K-nearest Neighbors (KNN), Gaussian Naive Bayes (GNB), Stochastic Gradient Descent (SGD), Linear Discriminant Analysis (LDA), Ridge, Lasso, and Elastic net.

The pre-trained artificial intelligence algorithm (or an artificial intelligence model) may be an algorithm designed (trained) to receive recorded video (or surgical image) as an input value and to output the surgical stage as an output value.

In this specification, the surgical stage output from the pre-trained artificial intelligence algorithm may be named the determined surgical stage or the inferred surgical stage.

The recording device 30 may link the recorded video to the determined surgical stage when the determined (inferred) surgical stage is determined to be a predetermined surgical stage (S230).

Moreover, the pre-trained artificial intelligence algorithm according to an embodiment of the present disclosure may perform various functions.

For example, the recording device 30 may delete a video portion, in which a non-surgical situation is recorded, from the recorded video by using the pre-trained artificial intelligence algorithm.

Furthermore, the recording device 30 may not record images corresponding to non-surgical situations by using the pre-trained artificial intelligence algorithm.

In addition, the recording device 30 may selectively record only images including a specific surgical process by using the pre-trained artificial intelligence algorithm.

For example, the recording device 30 may selectively record an angiographic image by using the pre-trained artificial intelligence algorithm.

Moreover, the recording device 30 may infer a surgical stage corresponding to the recorded video by using the pre-trained artificial intelligence algorithm.

In other words, the recording device 30 may input the recorded video into a pre-trained artificial intelligence algorithm to determine (infer) the surgical stage, and may determine whether the determined (inferred) surgical stage is a predetermined surgical stage.

The recording device 30 may link (or match) the recorded video to the inferred surgical stage based on the inferred surgical stage (i.e., when the inferred surgical stage is the predetermined surgical stage).

For example, when the inferred surgical stage is the predetermined surgical stage (e.g., a surgical stage requiring vascular and organ matching), the recording device 30 may link (or match) the recorded video to the inferred surgical stage.

The linked video may be a part of a video corresponding to the corresponding surgical stage among the recorded videos.

Also, the recording device 30 may pause recording of the video while linking the recorded video with the inferred surgical stage.

When the recorded video is linked to the inferred surgical stage, the recording device 30 may resume recording.

Furthermore, at least one of the recording device 30 and the server 100 may update the pre-trained artificial intelligence algorithm by using the recorded video.

To this end, the recording device 30 may transmit at least part of the recorded video to the server (S240).

The recording device 30 may segment the recorded video, and may transmit at least part of the segmented video to the server 100.

Here, the recording device 30 may segment the recorded video by using the pre-trained artificial intelligence algorithm.

The recording device 30 may recognize the surgical stage in the recorded video and may segment the recorded video based on the recognized surgical stage. Afterward, the recording device 30 may transmit some of the segmented video to the server 100 to be used to update the artificial intelligence algorithm, based on the importance of the predetermined surgical stage.

The server 100 may update the pre-trained artificial intelligence algorithm of the recording device by using the video received from the recording device 30 (S250).

In detail, the server 100 may update the pre-trained artificial intelligence algorithm by using at least part of the segmented video received from the recording device.

For example, the server 100 may perform machine learning by setting the received video as an input value and setting the surgical stage of the video as an output value. Afterward, the server 100 may update an artificial intelligence algorithm (an artificial intelligence model) through machine learning.

The server 100 may transmit the updated pre-trained artificial intelligence algorithm to the recording device 30.

Afterward, the server 100 may transmit the updated artificial intelligence algorithm to the recording device 30 such that the pre-trained artificial intelligence algorithm of the recording device 30 is updated.

In other words, the artificial intelligence surgical system according to an embodiment of the present disclosure may add an AI function to the recording device 30 to selectively perform recording in the recording device, or may perform surgical navigation.

Also, in the artificial intelligence surgical system according to an embodiment of the present disclosure, the recording device 30 may be linked with the server 100 such that the artificial intelligence model (artificial intelligence algorithm) in the recording device is updated by the server 100, and operation standards of the artificial intelligence model are set.

Moreover, in the artificial intelligence surgical system according to an embodiment of the present disclosure, the recording device 30 may control the artificial intelligence model to provide real-time video (surgical image) required for the surgical stage to be used for surgical navigation, and may match (link) and store the surgical stage and the recorded video (surgical image).

Figure 3:
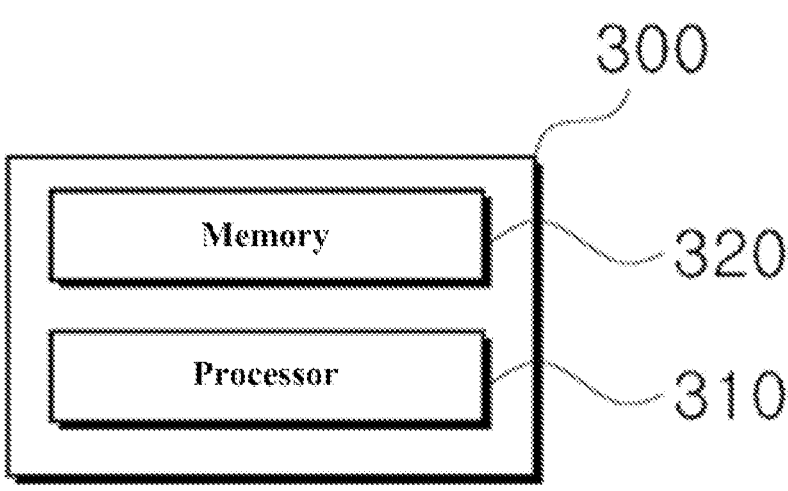
FIG. 3 is a diagram schematically showing a configuration of a device that performs a control method of an artificial intelligence surgical system.

FIG. 3 is a diagram schematically showing a configuration of a device that performs a control method of an artificial intelligence surgical system.

The device may be provided in the recording device 30 and/or the server 100.

Referring to FIG. 3, a processor 310 may include one or more cores (not illustrated), a graphic processing unit (not illustrated), and/or a connection path (e.g., a bus, or the like) through which a signal is transmitted and received with other components.

According to an embodiment, the processor 310 may perform the artificial intelligence surgical control method described in FIG. 2 by executing one or more instructions stored in a memory 320.

For example, when a device 300 is provided in the recording device 30, the processor 310 may execute one or more instructions stored in memory 320. Accordingly, the recording device records a surgical process as a video; the recording device inputs the recorded video to a pre-trained artificial intelligence algorithm and determines a surgical stage; the recording device links the recorded video to the determined surgical stage when it is determined that the determined surgical stage is a predetermined surgical stage; and, the recording device transmits at least part of the recorded video to the server.

For example, when the device 300 is provided in the server 100, the processor 310 may execute one or more instructions stored in memory 320. Accordingly, the server updates the pre-trained artificial intelligence algorithm of the recording device by using the video received from the recording device.

In the meantime, the processor 310 may further include Random Access Memory (RAM) (not illustrated) and Read-Only Memory (ROM) (not illustrated) that temporarily and/or permanently store a signal (or data) processed inside the processor 310. Furthermore, the processor 310 may be implemented in the form of a system on chip (SoC) including at least one of a graphic processor, RAM, and ROM.

Programs (one or more instructions) for the processing and controlling of the processor 310 may be stored in the memory 320. The programs stored in the memory 320 may be divided into a plurality of modules depending on functions.

The control method of an artificial intelligence surgical system according to an embodiment of the present disclosure may be implemented by a program (or an application) and may be stored in a medium such that the program is executed in combination with a computer being hardware.

Steps or operations of the method or algorithm described with regard to an embodiment of the present disclosure may be implemented directly in hardware, may be implemented with a software module executable by hardware, or may be implemented by a combination thereof. The software module may reside in a random access memory (RAM), a read only memory (ROM), an erasable programmable ROM (EPROM), an electrically erasable programmable ROM (EEPROM), a flash memory, a hard disk, a removable disk, a CD-ROM, or a computer-readable recording medium well known in the art to which the present disclosure pertains.

Although an embodiment of the present disclosure are described with reference to the accompanying drawings, it will be understood by those skilled in the art to which the present disclosure pertains that the present disclosure can be carried out in other detailed forms without changing the scope and spirit or the essential features of the present disclosure. Therefore, the embodiments described above are provided by way of example in all aspects, and should be construed not to be restrictive.

According to an embodiment of the present disclosure, an optimized surgical navigation information may be provided by linking (matching) a video corresponding to a specific surgical stage among a surgical video recorded by using an artificial intelligence algorithm to the specific surgical stage.

Moreover, an artificial intelligence surgical system and a control method therefor may be provided to update the artificial intelligence algorithm with an optimized state by using the recorded video.

Effects of the present disclosure are not limited to the effects mentioned above, and other effects not mentioned will be clearly understood by those skilled in the art from the following description.

While the present disclosure has been described with reference to embodiments, it will be apparent to those skilled in the art that various changes and modifications may be made without departing from the spirit and scope of the present disclosure. Therefore, it should be understood that the above embodiments are not limiting, but illustrative.

What is claimed is:

1. An artificial intelligence surgical system comprising:

a recording device configured to record a surgical process as a video and to input the recorded video to a pre-trained artificial intelligence algorithm to determine a surgical stage;

a server configured to update the pre-trained artificial intelligence algorithm of the recording device by using the video received from the recording device; and a surgical robot comprising: a plurality of surgical arms; and at least one camera coupled with at least one surgical arm of the plurality of surgical arms, wherein the recording device comprises a display configured to play a video captured by the at least one camera of the surgical robot, wherein the recording device is configured to:

infer a surgical stage corresponding to the recorded video by using the pre-trained artificial intelligence algorithm;

link the recorded video with the surgical stage based on the surgical stage; and link the recorded video with the surgical stage when the surgical stage is a surgical stage requiring vascular and organ matching, wherein the recording device is configured to:

segment the recorded video based on the surgical stage; and transmit a part of the segmented video to the server, based on an importance level of the surgical stage, wherein the server is configured to:

update the pre-trained artificial intelligence algorithm by using the part of the segmented video, received from the recording device, wherein the server performs machine learning by setting the part of the segmented video as an input value and setting the surgical stage as an output value, and update the pre-trained artificial intelligence algorithm through the machine learning; and transmit the updated pre-trained artificial intelligence algorithm to the recording device, and wherein the recording device is configured to, based on the updated pre-trained artificial intelligence algorithm, selectively record an angiographic image, provide a surgical image required for the surgical stage to be used for a surgical navigation, and link and store the surgical stage and the surgical image.

2. The artificial intelligence surgical system of claim 1, wherein the recording device is configured to:

delete a video portion, in which a non-surgical situation is recorded, from the recorded video by using the pre-trained artificial intelligence algorithm.

3. The artificial intelligence surgical system of claim 1, wherein the recording device is configured to:

pause recording of the video while linking the recorded video with the surgical stage.

4. A control method of an artificial intelligence system including a recording device, a server, and a surgical robot, the method comprising:

recording, by the recording device, a surgical process as a video;

inputting, by the recording device, the recorded video to a pre-trained artificial intelligence algorithm and determining a surgical stage;

when it is determined that the determined surgical stage is a predetermined surgical stage, linking, by the recording device, the recorded video to the determined surgical stage;

transmitting, by the recording device, at least part of the recorded video to the server;

updating, by the server, the pre-trained artificial intelligence algorithm of the recording device by using the video received from the recording device, wherein the surgical robot comprises a plurality of surgical arms; and at least one camera coupled with at least one surgical arm of the plurality of surgical arms, and the recording device comprises a display;

playing, by the display of the recording device, a video captured by the at least one camera of the surgical robot;

inferring, by the recording device, a surgical stage corresponding to the recorded video by using the pre-trained artificial intelligence algorithm;

linking, by the recording device, the recorded video with the surgical stage based on the surgical stage;

linking, by the recording device, the recorded video with the surgical stage when the surgical stage is a surgical stage requiring vascular and organ matching;

segmenting, by the recording device, the recorded video, based on the surgical stage;

transmitting, by the recording device, at least part of the segmented video to the server, based on an importance level of the inferred surgical stage;

updating, by the server, the pre-trained artificial intelligence algorithm by using the at least part of the segmented video, received from the recording device, wherein the server performs machine learning by setting the part of the segmented video as an input value and setting the surgical stage as an output value, and update the pre-trained artificial intelligence algorithm through the machine learning; and transmitting, by the server, the updated pre-trained artificial intelligence algorithm to the recording device, wherein the recording device, based on the updated pre-trained artificial intelligence algorithm, selectively records an angiographic image, provides a surgical image required for the surgical stage to be used for a surgical navigation, and links and stores the surgical stage and the surgical image.

5. The method of claim 4, further comprising:

deleting, by the recording device, a video portion, in which a non-surgical situation is recorded, from the recorded video by using the pre-trained artificial intelligence algorithm.

6. The method of claim 4, further comprising:

pausing, by the recording device, the video while linking the recorded video with the inferred surgical stage.

7. A non-transitory computer-readable recording medium storing a computer program in combination with a computer that is a piece of hardware to execute the method of claim 4.

* * * * *